United States Patent [19]
Wong et al.

[11] Patent Number: 4,773,428
[45] Date of Patent: * Sep. 27, 1988

[54] APPARATUS AND METHOD FOR MEASURING VISCOELASTIC PROPERTIES OF MAMMALIAN CERVICAL MUCOUS

[75] Inventors: Jacob Y. Wong, Santa Barbara; Pierre Khuri-Yakub, Palo Alto; M. Edward Motamedi, Thousand Oaks; Marcus Y. Wong, Los Angeles, all of Calif.

[73] Assignees: Hibshman Corporation, Santa Barbara; Adamtek Corporation, San Luis Obispo, both of Calif.

[ * ] Notice: The portion of the term of this patent subsequent to Sep. 8, 2004 has been disclaimed.

[21] Appl. No.: 786,064

[22] Filed: Oct. 10, 1985

Related U.S. Application Data

[63] Continuation-in-part of Ser. No. 661,226, Oct. 15, 1984, Pat. No. 4,691,714.

[51] Int. Cl.⁴ .............................................. A61B 5/04
[52] U.S. Cl. ......................................... 128/738; 73/54
[58] Field of Search ...................... 374/117; 128/738; 73/54, 59, 60

[56] References Cited

U.S. PATENT DOCUMENTS

| | | | |
|---|---|---|---|
| 3,844,273 | 10/1974 | Polson | 128/738 |
| 3,844,276 | 10/1974 | McDougall | 128/642 |
| 3,979,945 | 9/1976 | Kopito et al. | 73/60 |
| 3,982,423 | 9/1976 | Schuster | 73/54 |
| 3,986,388 | 10/1976 | Stolzy | 73/59 |
| 4,117,716 | 10/1978 | Simon | 73/32 A |
| 4,224,949 | 9/1980 | Scott et al. | 128/734 |
| 4,247,758 | 1/1981 | Rodrian | 377/6 |
| 4,249,418 | 2/1981 | Ebata | 374/117 |
| 4,387,724 | 6/1983 | Zartman | 128/736 |
| 4,399,441 | 8/1983 | Vaughan et al. | 342/50 |

OTHER PUBLICATIONS

Dos, P. et al., "A Self-Transmitting SAW Pressure Transducer", Jrnl. of Bioengrg., vol. 2, No. 1-2, pp. 27-32, Apr. 1978.
Goldstein, N. N. et al., "Foundations of Physiological Instrumentation", Charles C. Thomas Publ., Springfield, Ill., ©1979, pp. 172-173.

*Primary Examiner*—Francis J. Jaworski
*Attorney, Agent, or Firm*—Lyon & Lyon

[57] ABSTRACT

An apparatus and method for measurement of viscoelastic properties of mammalian cervical mucous by generating a bulk acoustic wave which is reflected off of a face in contact with the mucous whereby an output which is a function of the viscoelastic properties is generated based upon at least one characteristic of the reflected bulk wave.

57 Claims, 10 Drawing Sheets

APPARATUS AND METHOD FOR MEASURING VISCOELASTIC PROPERTIES OF MAMMALIAN CERVICAL MUCOUS

RELATED APPLICATION

This application is a continuation-in-part of U.S. Pat. application Ser. No. 661,226, filed Oct. 15, 1984, and now U.S. Pat. No. 4,691,714 issued Sept. 7, 1987, the disclosure of which is incorporated herein by reference.

BACKGROUND OF THE INVENTION

1. Field of the Invention

The field of the present invention relates generally to an apparatus and method for determining viscoeleastic properties of mammalian cervical mucous. For humans, the determination of the viscoelastic properties of the mucous can be used to predict and indicate inception and presence of ovulation for increasing the likelihood of conception or for contraception. For livestock and other mammals, the determination can be used to detect estrus for breeding management.

2. Description of the Prior Art

Many forms of family planning require a woman wanting to avoid pregnancy to identify her fertile period so she can practice sexual abstinence or use other means or birth control during this period. On the other hand, many marginally fertile couples desiring pregnancy have a higher probability of conceiving if sexual intercourse is confined to the woman's fertile period or if the capsules abstain for several days before the period. Ovulation is the key event in the female fertile period. The fertile period for women typically consists of only about four days in the menstrual cycle: three days preceding ovulation (necessitated by sperm survival), and one day after ovulation (necessitated by ovum survival).

It is well known that the rheology of cervical mucous undergoes significant changes at the onset and throughout the female fertile period. See Schuster, U.S. Pat. No. 3,982,423 (1976). During the immediate pre-ovulatory phase and the rest of the menstrual cycle, the mucous becomes less abundant and no longer possesses certain threadability characteristics. In rheological terms, the muscous is highly viscous except during the ovulation phase of the menstrual cycle. If one can determine the changes in the viscoelastic properties of cervical mucous that occur before the onset of ovulation, it is possible to pinpoint the female fertile period.

Accordingly, there exists a need for a simple, accurate and easy-to-use device which women can use in the comfort and privacy of their own home to identify their fertile period to either increase the likelihood of conception or to practice birth control by either sextual abstinence or another form of birth control.

In the so-called Billings method of contraception by periodic abstinence, a woman is taught to identify the precise characteristics of cervical mucous produced at various states of her menstrual cycle and their relationship to her fertile and infertile days. The method tends to be subjective and lacks quantitative precision so it tends to be unreliable. The more widely practiced Basal body temperature method uses the changes in daily temperature taken immediately at awakening to identify the temperature shift that occurs at or shortly after ovulation. To be effective, the woman must adhere to a highly repetitive routine before the daily temperature taking because any restlessness, motion, infection or mental stress causes small temperature shifts, which can result in incorrect data. The Sympto-Therman method charts temperature changes and changes in volume and viscosity of cervical muscous and teaches women to recognize such subjective symptoms of ovulation as intermenstrual pain. This method fares no better because the measurements lack precision and objectivity.

Kopito, U.S. Pat. No. 3,979,946 (1976) and the aforementioned Schuster patent both teach devices designed to give quantitative measurements of rheological properties of cervical mucous, including its viscoelastic properties, but both are complex and difficult to use and are mechanical devices subject to error. In addition, the mucous is not tested in vivo. Thus, such devices are not suitable for widespread use by women in the comfort and privacy of their own home.

In addition to the needs of women and couples who wish to identify the inception and presence of ovulation in the human female, the detection of the inception and presence of ovulation in other mammals is also important for the purpose of breeding. Thus, for example, detecting estrus in cattle is important, but also difficult, for the farmer. Failure to detect estrus at the proper time means delayed breeding and long calving intervals, which result in a decreased production of milk and beef. The problem is further complicated as herd size increases because it is difficult to observe more cows. Various techniques have been advanced for the detection of estrus in cattle. For example, Scott, U.S. Pat. No. 4,224,949 (1980), and McDougall, U.S. Pat. No. 3,844,276 (1974), test electrical resistance of cervical mucous using a bovine vaginal probe. Rodian, U.S. Pat. No. 4,247,758 (1981), measures movements of animals which are said to be increased during estrus. Zartman, U.S. Pat. No. 4,387,724 (1983), measures long-term deep body temperature. However, none of these techniques utilizes changes in rheological parameters such as viscosity for bovine cervical mucous at the onset and throughout the bovine estrus period. Thus, there exists a need for a simple and quick apparatus and method for accurately detecting the inception and presence of ovulation in mammals, such as cattle, which are bred.

SUMMARY OF THE INVENTION

In the present invention, viscoelastic properties of mammalian cervical mucous are determined by an apparatus and method which utilize a bulk acoustic wave to generate an output which is a function of said properties.

When mammalian cervical mucous is measured according to the present invention, the mucous is exposed to a first face of an inert slab, a bulk wave is generated in the inert slab toward the first face and an output based upon at least one characteristic of the bulk wave, after it has reflected from the first face, is generated. In one embodiment according to the present invention, the amplitude of the output is compared to a reference output. In another embodiment according to the present invention, changes in Q individually modulated peaks of the output are measured.

When an apparatus is used in accordance with a method of the present invention, in vivo measurements of viscoelastic properties of cervical mucous can be obtained in a simple, quick and efficient manner. The measurement is quantitative and essentially error-free. Also, because of the magnitude of change in viscoelastic properties during ovulation, the measurement will provide accurate information to predict and indicate inception and the presence of ovulation. Further, unlike temperature, viscoelastic properties will not be subject to rigid procedures to ensure meaningful results.

An apparatus according to the present invention is safe and simple to use. Because the apparatus is compact, it can be used for it vivo, measurements.

Because the vaginal probe can be made out of plastic with a fused silica sensing element imbedded in it, no current or voltage carrying parts are exposed to the user. There is, therefore, complete electrical isolation between the user and the power source of the probe. The amount of RF power coupled to the vaginal wall near the cervical os during the in vivo measurement is less than 100 microwatts, which poses no radiation threats of any kind to the user.

As the device is designed to be inserted into the vagina, this arrangement provides a clean and inert surface which is smooth and free from any physical attachments and can be washed and made sterile.

When an apparatus is used by a human female, the apparatus can be used in the comfort and privacy of the woman's home.

Accordingly, it is a primary object of the present invention to provide an apparatus of mammalian cervical mucous to predict and indicate inception and the presence of ovulation.

This and further objects and advantages will be apparent to those skilled in the art in connection with the drawings and the detailed description of the preferred embodiments set forth below.

DETAILED DESCRIPTION OF THE PREFERRED EMBODIMENTS

Figure 1A:
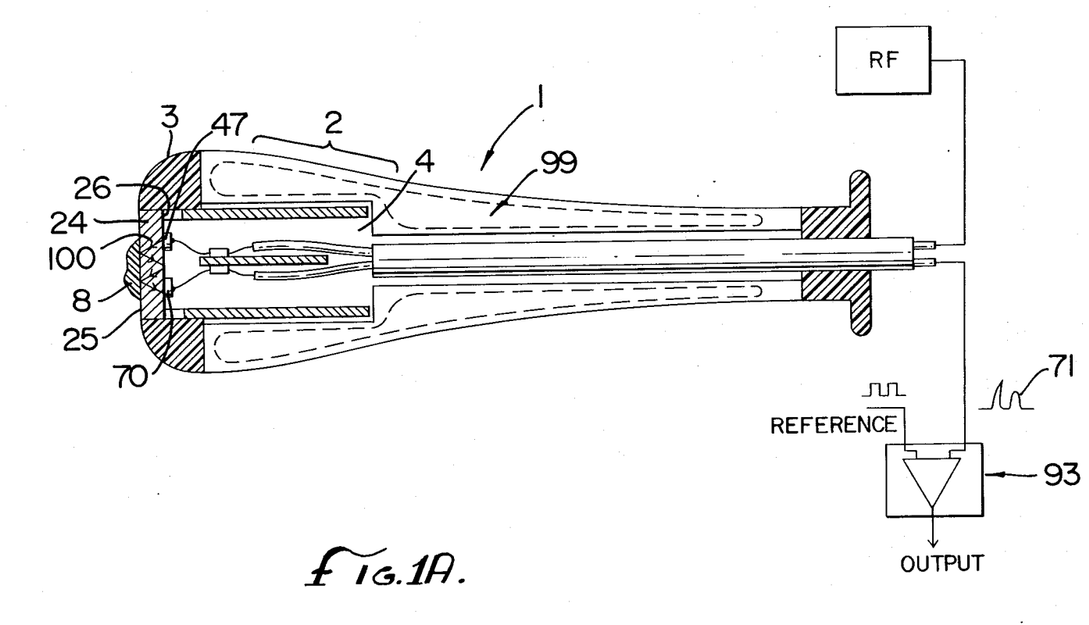
FIG. 1A is a partially schematic cross-sectional view of one exemplary embodiment of the ovulation testing apparatus of the present invention.

A preferred embodiment of an apparatus according to the present invention, generally designated as 1, is depicted in FIG. 1A. The device is comprised of a probe housing, generally designated as 2, an inert slab 24 held in the probe housing 2, the inert slab having a first face 25 exposable to mucous 8, an acoustic wave generating means, generally designated as 47, located on the second face 26 of the inert slab 24 for generating a bulk wave 100 toward the first face 25 and a sensing means, generally designated as 70, located on the inert slab 24 for generating an output 71 based upon at least one characteristic of the bulk wave 100 after it has reflected from the first face 25. The output 71 is a function of viscoelastic properties of the mucous 8. Although the location of the inert slab 24 in the probe housing 2 may vary, it is generally desirable that the first face 25 of the inert slab 24 is approximately flush with the external wall 3 of the probe housing 2 so as to create a smooth surface which will not damage any tissue when the device 1 is used for in vivo testing of mammalian cervical mucous.

In utilizing an apparatus in a method according to the present invention, the first face 25 of the inert slab 24 is placed into contact with the mucous 8. Once the mucous 8 is in contact with the first face 25, a bulk wave 100 is generated toward the first face 25. After the bulk wave 100 reflects from the first face 25, an output 71 is generated based upon at least one characteristic of the bulk wave 100 after it has reflected from the first face 25. The output 71 is a function of viscoelastic properties of the mucous 8. While the present invention contemplates a device suitable for in vivo testing, it would also work for in vitro testing of mammalian cervical mucous. In designing a device 1 in accordance with present invention for in vivo measurement, the probe housing 2 should be shaped for insertion into a mammalian vagina for positioning the first face 25 in contact with the cervical mucous 8, and more particularly, for positioning the first face 25 into contact with the cervical os and the device 1 may contain a means, such as a collapsible cavity in probe housing 2, generally designated as 99, for positioning the first face 25 into contact with the cervical mucous 8. Because the positioning of the cervical os will vary in different mammalian vaginas, and in fact some vaginas may contain sufficient cervical mucous so as not to make the placement of the first face 25 close to the cervical os a necessary prerequisite to an accurate reading, a physical examination of the mammalian vagina may be necessary so as to identify what shape of device 1 is necessary for the particular subject.

Figure 2:
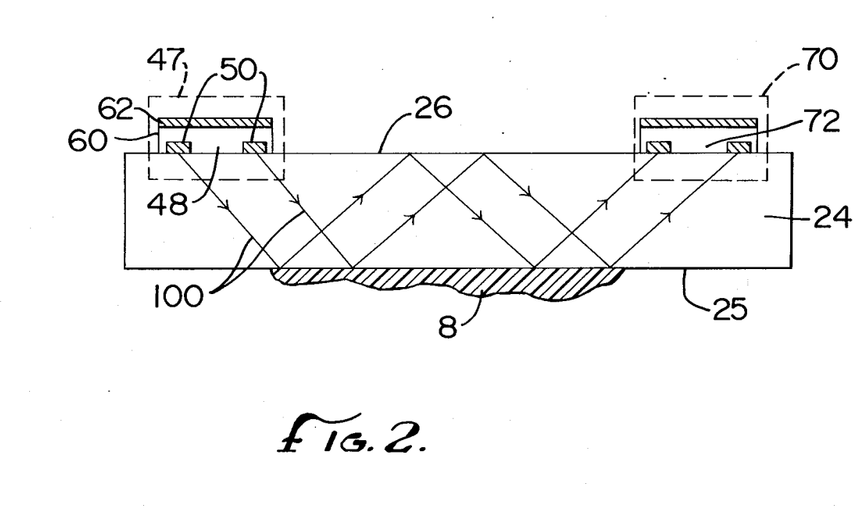
FIG. 2 is a partially schematic sectional view of the sensing element of the present invention depicted in FIG. 1A in side elevation. The figure also shows the acoustic wave propagation through the fused silica slab in accordance with the present invention.
Figure 3:
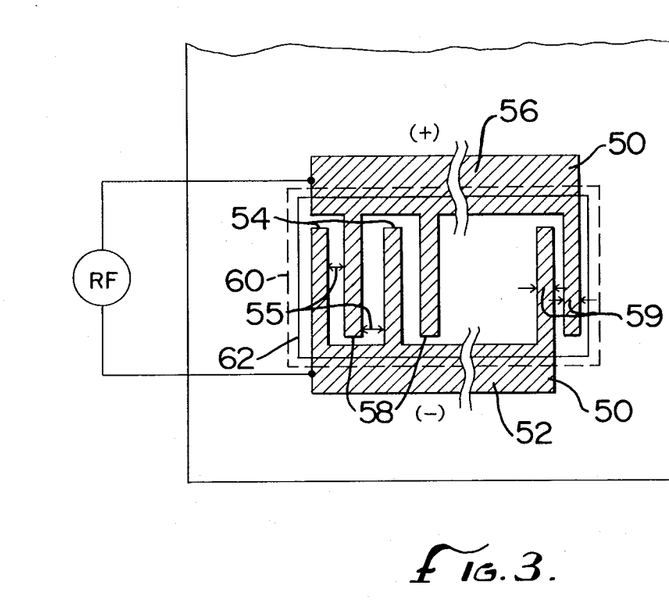
FIG. 3 is a top schematic view of one of the two interdigital transducers of the present invention, which is used to generate or detect acoustic waves.

A particularly preferred embodiment of the present invention is partially depicted in FIG. 2 wherein the device 1 utilizes an acoustic an acoustic wave generating means 47 on the second face 26 of the inert slab 24 for generating a bulk wave 100 toward first face 25. In this device, it is particularly preferred that the second face 26 is parallel and opposite to the first face 25 and the slab is formed of a non-piezoelectric material. The acoustic wave generating means 47 may comprise a first interdigital transducer 48. A suitable first interdigital transducer 48 can be constructed of pair of electrodes 50, each of the pair of electrodes 50 being adjacent to each other and in contact with the second face 26. As is set forth in greater detail in FIG. 3, each of the pair of electrodes 50 can be comprised of a first base 52 having a first plurality of equally spaced arms 54 and a second base 56 having a second plurality of equally spaced arms 58, the spacing 55 between the first and second plurality of equally spaced arms 54 and 58 being identical, the first and second plurality of equally spaced arms 54 and 58 being intertwined but not in direct contact with each other. The width 59 of the first and second plurality of equally spaced arms 54 and 58 and the spacing 55 can be selected such that the acoustic wave generating means 47 generates a bulk wave 100 in the inert slab 24 such that the bulk wave 100 reflects first off of the first face 25, then off of the second face 26, then reflects again off of the first face 25, and then to a receiving means 70 as depicted in FIG. 2. Receiving means 70 may also comprise a second interdigital transducer 72. Since the second interdigital transducer 72 may be comprised in identical fashion to the first interdigital transducer 48, a detailed drawing of the second interdigital transducer 72 has not been set forth. The receiving means for second interdigital transducer 72 is preferably located on the second face 26.

In addition to the pair of electrodes 50 (see FIG. 2), the interdigital transducer 48 may further comprise a layer of piezoelectric material 60 which is in direct contact with the pair of electrodes 50 and is also in direct contact with the inert slab 24. The layer of piezoelectric material 60 may or may not completely cover the pair of electrodes 50. The first interdigital transducer 48 may also further comprise a metalization layer 62 which is in direct contact with the layer of piezoelectric material 60 and may actually completely cover said layer of piezoelectric material. The metalization layer 62 functions to enhance the coupling of acoustic energy into the inert slab 24. In this preferred embodiment, the output 71 is generated by the receiving means 70 on the slab 24 in the path of the bulk wave 100 after it reflects from the first face 25 (see FIG. 1A). The amplitude of the output 71 is measured and compared to a reference output is a comparison means generally depicted as 93, which may be a circuit, or by the difference between the output 71 and the reference output either of which is a function of viscoelastic properties of the mucous 8 in contact with the first face 25.

Figure 1B:
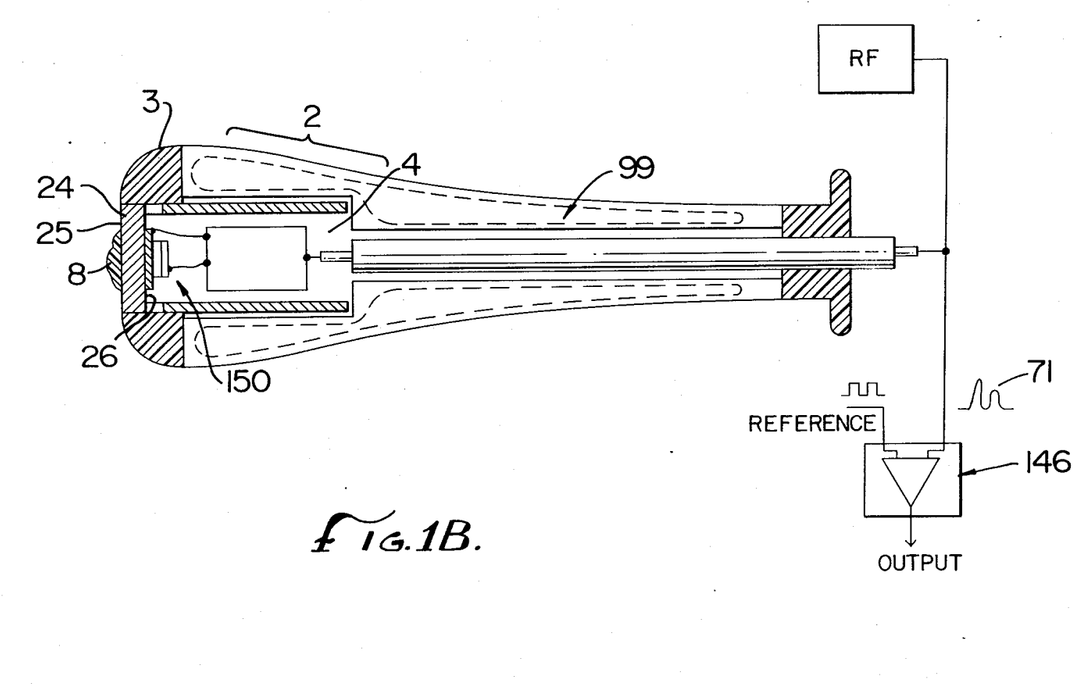
FIG. 1B is a partially schematic cross-sectional view of another exemplary embodiment of the ovulation testing apparatus of the present invention.
Figure 4:
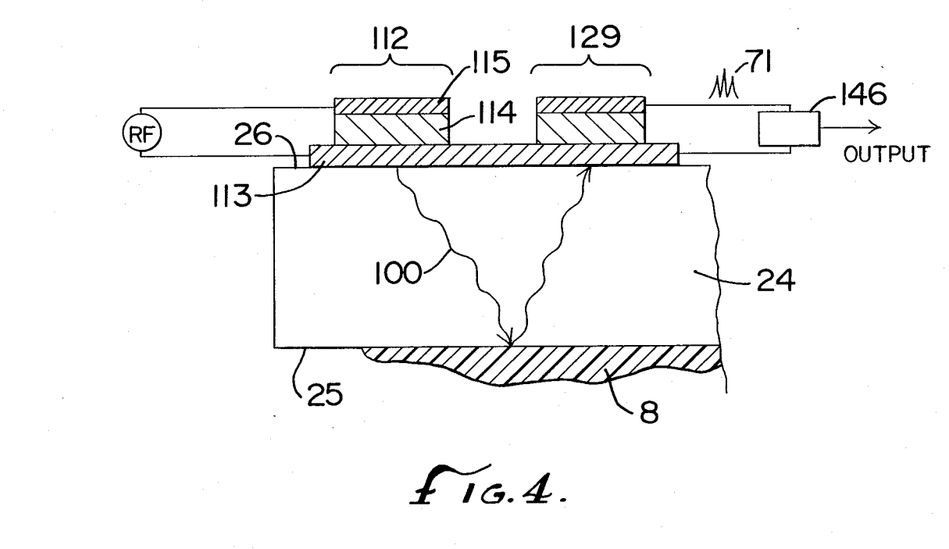
FIG. 4 is a side elevation view of an alternative bulk acoustic wave resonator in accordance with the present invention. This embodiment employs separate acoustic wave resonators as generator and detector of acoustic waves.
Figure 5:
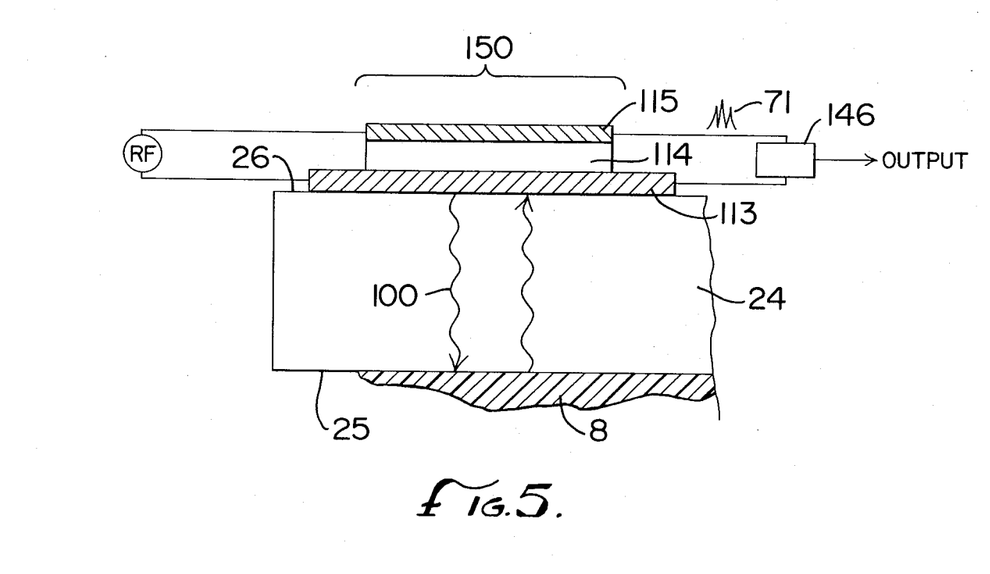
FIG. 5 is a side elevation view of an alternative bulk acoustic wave resonator in accordance with the present invention. This embodiment uses the same acoustic wave resonator as the generator and detector of acoustic waves.

In a second preferred embodiment of the present invention, depicted in FIG. 4, a resonator means 112 is utilized to generate a bulk wave 100 in the inert slab 24. The resonator means 112 is acoustically coupled to the slab 24 and a detection means 129 is located on the slab 24 for generating an output 71 from a plurality of resonating waves which are formed after the resonator means 112 generates the bulk wave 100 in the slab 24 toward the first face 25. In this especially preferred embodiment, the resonator means 112 and the detection means 129 are one and the same as shown in FIG. 5. The common resonator means 150 which first acts as a generator and then as a detector is comprised of a first metalizing layer 113 in direct contact with the slab 24, a second metalizing layer 115, and an intermediate layer of piezoelectric material 114 which is sandwiched in between and in direct contact with the first and second metalizing layers 113 and 115. As with the first preferred embodiment, it is preferred that the slab 24 is comprised of a non-piezoelectric material, such as fused silica. While the second metalizing layer 115 may cover the entire intermediate layer of piezoelectric material 114, it should not be in direct contact with the first metalizing layer 113. It is also preferred that the common resonator means 150 is coupled to the second face 26 of the slab 24 which is parallel and opposite the first face 25. The common resonator means 150 communicates with a measurement means 146 which measures changes in Q of individually modulated peaks of the output 71 whereby changes in Q are a function of viscoelastic properties of the mucous 8 in contact with the first face 25. The measurement means 146 may be in direct physical contact with the common resonator means 150 or may receive data from the common resonator means 150 from a method of communication in which there is no direct contact between the common resonator means 150 and the measurement means 146. As an example, the common resonator means 150 could generate an electrical signal which could be picked up by the measurement means 146 or the common resonator means 150 could display an output which could then be manually fed into the measurement means 146. However, in an especially preferred embodiment, the common resonator means 150 and the measurement means 146 are in direct electrical contact inside of an internal cavity 4 of the probe housing 2 (see FIG. 1B) to form a simple and compact device which can be utilized for in vivo testing of mammalian cervical mucous.

In both of the above described preferred embodiments of an apparatus according to the present invention, the sensing means 70 or common resonator means 150 is connected to an inert slab 24. By an inert slab, it is meant a slab which will not undergo a chemical reaction with the mammalian cervical mucous. One example of such an inert slab is a slab comprised of fused silica. The acoustic wave generating means 47 or common resonator means 150 is generally fabricated on the second face 26 of the slab 24 for generating a bulk acoustic wave 100 toward the first face 25. A receiving sensing means 70 or common resonator means 150 is fabricated on the slab in the path of the bulk wave 100 after it reflects from the first face 25. The viscoelastic properties of the cervical mucous in contact with the first face 25 control the amplitude of the output 71 which may be measured by a circuit attached to a receiving transducer which measures the amplitude of the output and compares the output to a reference output.

In order to provide an even more detailed description of the present invention, set forth below, by way of example only, is a description of a physical embodiment which has been constructed for testing by the applicants. In addition, in order to provide a more thorough teaching of the present invention, the operable principles of the instant invention as now known are discussed in connection with said physical embodiment.

Figure 6:
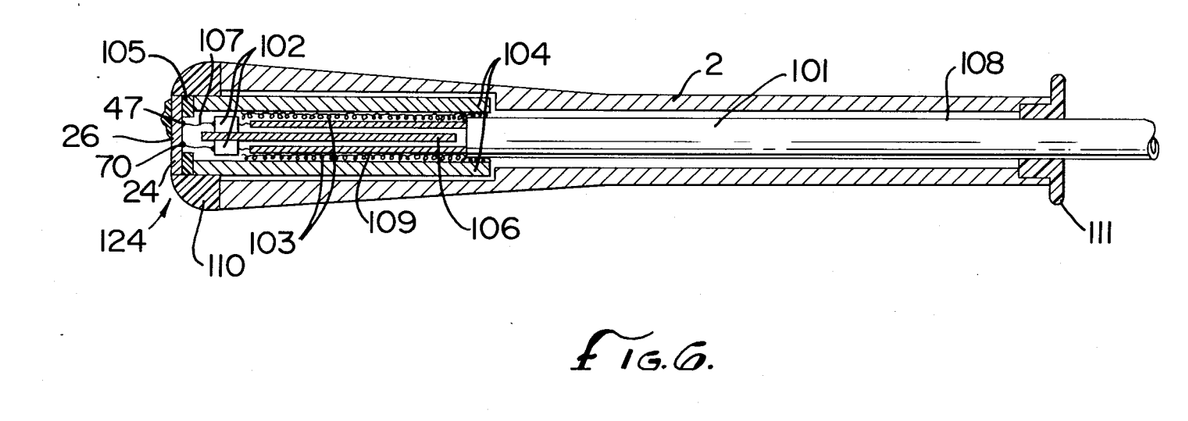
FIG. 6 is a partially schematic cross-sectional view of an actually constructed ovulation testing apparatus of the present invention.

A vaginal probe was constructed according to the preferred embodiment shown generally in FIG. 1A, which is shown in greater detail in FIG. 6. The construction of the vaginal probe is carried out in three steps.

First, an outer housing 2 in the form of a long cylindrical shell is injection molded out of an FDA approved grade of polypropylene suitable for insertion into human internal cavities such as the vagina.

Second, the transducer support structure 101 comprising the sensing element 124, impedance matching electronic components 102 and coaxial cables 103 is physically assembled as a unit which fits snugly inside the outer housing shell 2 as shown in FIG. 6. The sensing element 124, in the form of a thin square fused silica slab, is rigidly supported by one end of a square hollow brass conduit 104 through the use of an intermediate brass collar 105. The end of the hollow brass conduit 104 is soldered to the brass collar 105 which in turn is soldered to a gold guard ring (not shown in FIG. 6) on face 26 of the sensing element 124. The hollow brass conduit 104 has a center copper partition wall 106 which is electrically grounded for isolating the two signal channels from the sensing element 124. One of these two channels is for the generation of bulk acoustic waves and the other is for the detection of them. Both the generator and detector for these acoustic waves are interdigital transducers as will be described in more detail below. The two channels of the sensing element 124 are respectively connected electrically to impedance matching components 102 on opposite sides of the partition wall 106 using gold wire 107. They are then connected to separate coaxial cables 103 bundled together and protected by a sheath 108 outside of the hollow brass conduit 104 for respective signal outputs. The coaxial cables 103 together with the impedance matching components 102 are potted with a silicone elastomer 109, sold under the trademark "RTV", inside the hollow brass conduit 104 for added structural integrity and electrical isolation.

Third, the transducer support structure 101 is fitted snugly inside the outer housing shell 2 and the entire vaginal probe is sealed against liquids and/or gases via injection molding the tip 110 and the probe end 111 with polypropylene as shown in FIG. 6. The electronic circuits which are used to drive the acoustic wave generator (in the form of an interdigital transducer 47) and to process the signals from the acoustic wave detector (in the form of another interdigital transducer 70) are housed externally to the vaginal probe (not shown in FIG. 6). They are electrically connected to the sensing element 124 via the coaxial cables 103 with sheath 108 protruding from the molded probe end 111.

Figure 7:
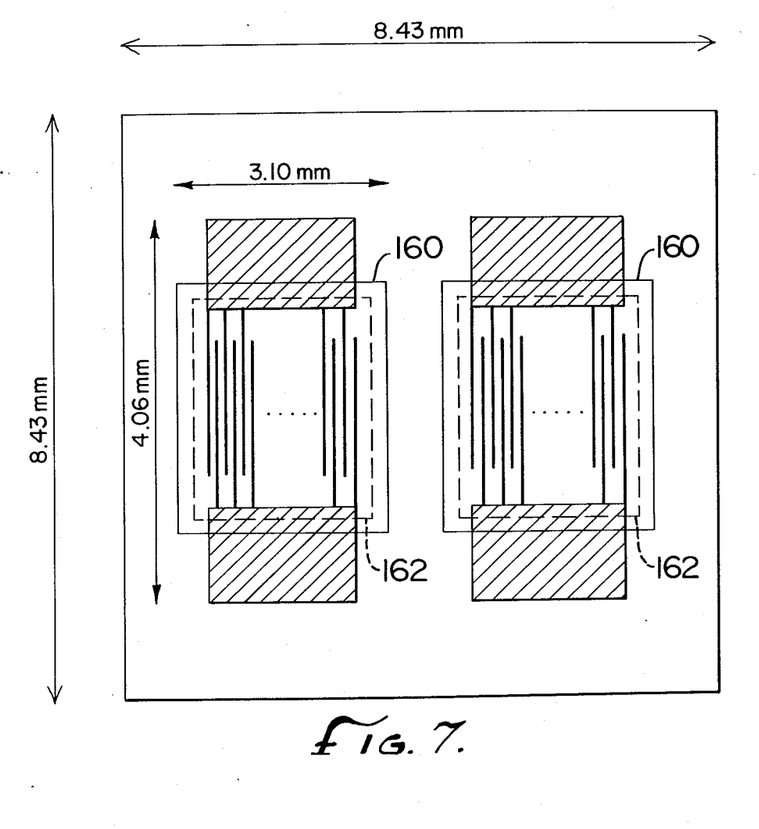
FIG. 7 is a top schematic view of an actually constructed sensing element showing the two interdigital transducers fabricated on a thin slab of fused silica. The two interdigital transducers are used respectively to generate and detect bulk acoustic waves in accordance with the present invention.

The sensing element 124 of the constructed vaginal probe shown schematically in FIG. 6 is fabricated out of a thin fused silica plate approximately 38.1×38.1 mm in area and 0.635 mm thick. Each plate yields a total of sixteen (16) sensing elements 124. Each sensing element 124 comprise two identical interdigital transducers. The plate is first polished parallel and flat to stipulated dimension. It is then cleaned for patterning sixteen sensing elements 124, each of which comprises two identical interdigital transducers having parameters shown in Table 1 and depicted schematically in FIG. 7. Each of the two interdigital transducers which together constitute the sensing element 124 is approximately 3.10×4.06 mm in area and has forty (40) arms with an effective length of 1.52 mm. The dimensions of the sensing element 125 comprising two interdigital transducers are approximately 8.43×8.43 mm.

TABLE 1

| | |
|---|---|
| Substrate thickness | 0.635 mm |
| Spatial wavelength | 0.025 mm |
| Interdigital transducer electrode pairs | 40 |
| Effective electrode length | 1.520 mm |
| Device size | 6.20 × 4.06 mm |
| Surface wave center frequency | 105 MHz |
| One-bounce angle, $\theta_1$ | 22.3° |
| Two-bounce angle, $\theta_2$ | 39.3° |
| Shear wave wavelength | 0.020 mm |
| Shear wave center frequency | 194 MHz |

TABLE 1-continued

| | |
|---|---|
| ZnO film thickness | 6.4 microns |
| Metal film thickness | 2,000 Å |

The interdigital transducers are fabricated out of Cr/Au metalization and patterned using a standard photolithographic "lift-off" technique. Once the interdigital transducers are formed, a layer of zinc oxide 6.4 microns thick is deposited over the entire fused silica plate via sputtering in a reactive atmosphere from a zinc target. The method used in depositing the ZnO layer is described in greater detail in B. T. Khuri-Yakub et al., "Reactive Magnetron Sputtering of ZnO." J. Appl. Phys. 52(7) July, 1981, the disclosure of which is specifically incorporated herein by reference. Next, a second photolithographic step is performed to deposit and pattern gold metallization on top of the ZnO in registration with the forty (40) arms of each of the pair of electrodes of each of the interdigital transducers (see FIG. 7). Finally, another photolithographic step is carried out to define the isolated ZnO islands 160 over each of the interdigital transducers. The unwanted ZnO layer elsewhere is etched away via a dilute solution of hydrochloric acid. After all these processing steps, the fused silica plate is diced to yield sixteen (16) individual sensing elements 124.

Figure 8:
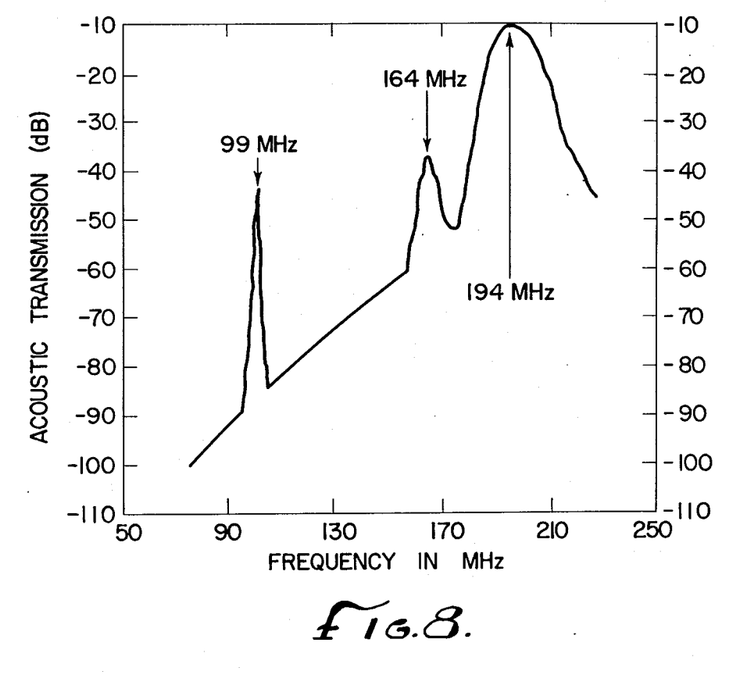
FIG. 8 is a measured graph for an actually constructed sensing element showing the acoustic insertion loss as a function of frequency.

FIG. 8 shows the signal loss (received/generated) of the fabricated sensing element 124 having the dimensions set forth in Table 1 as a function of the frequency in the RF range. The peak at 99 MHz is due to the surface acoustic wave. The peak at 164 MHz is due to the single reflection bulk wave (not shown in FIG. 2). The bulk acoustic wave 100 making two reflections causes the strongest peak at 194 MHz.

Figure 9:
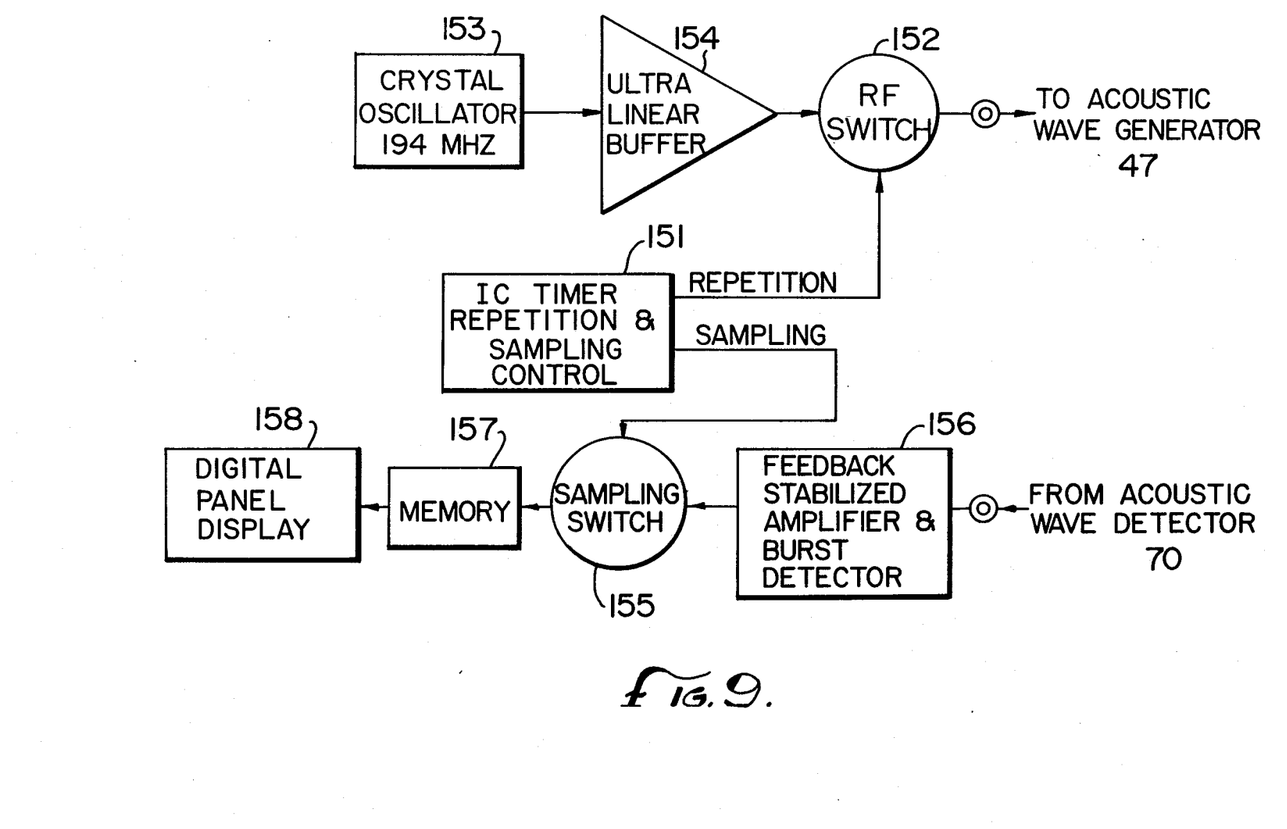
FIG. 9 is a schematic drawing of an actually constructed circuit used for the time sequential generation and detection of the twice-reflected bulk acoustic waves at 194 MHz. The amplitude of the output is a function of the viscoelastic property of the cervical mucous applied to the sensing element.

The block diagram of an electronic signal processing circuit used to measure the relative amplitudes of the acoustic waves reflected from first surface 25 of sensing element 124 (see FIG. 6) is shown schematically in FIG. 9. A timer circuit 151 controls an RF switch 152 which feeds an RF voltage pulse generated by a crystal oscillator 153 and an ultra linear buffer amplifier 154 to the acoustic wave generator 47. The same timer circuit 151 also controls a sampling switch 155 for gating the output from the acoustic wave detector 70 after a feedback stabilized amplifier and burst detector 156. The output from the sampling switch 155 which measures the amplitude of the acoustic wave reflected from the first surface 25 of the sensing element 124 (see FIG. 6) is sampled and held by a memory circuit 157 before it is displayed by a digital panel meter 158.

When liquid samples having various viscosity values at room temperature (22° C.) are placed in contact with first face 25, the detected amplitude for the bulk acoustic wave 100 that makes two reflections (namely at 194 MHz) varies as shown in Table 2, which also shows the actual viscosity.

TABLE 2

| Sample | Viscosity (22° C.) Centipoises | Relative Magnitude | Relative Amplitude (dB) |
|---|---|---|---|
| Air | 0 cp | 1.0 | 0 (reference) |
| Ethylene glycol | 20 cp | 0.54 | −5.38 dB |
| Glycerine | 1,490 cp | 0.41 | −7.74 dB |
| Honey | 9.1 × $10^{15}$ cp | 0.22 | −13.23 dB |

Because the "average" viscosity of human cervical mucous changes from values of several tens of thousands of centipoises during normal times to a low of only a few hundred centipoises during the ovulation period, the device of the present invention is capable of detecting sufficient changes of viscosity values to detect ovulation. Absolute viscosity values assists in predicting the onset of ovulation, but the circuitry necessary to calculate absolute viscosity can be directed to a storage medium so that trends in rate of change of the viscosity values rather than the absolute values can be used for determining the beginning of ovulation.

Various other modifications and changes may be made in the configuration described above that come within the spirit of the invention. The invention embraces all such changes and modifications coming within the scope of appended claims.

We claim:

1. A device suitable for measurement of viscoelastic properties of mammalian cervical mucous, comprising:
   a probe housing;
   an inert slab held in the probe housing, the inert slab having a first face exposable to the mucous, the probe housing being shaped for insertion into a mammalian vagina for positioning the first face in contact with the cervical mucous;
   acoustic wave generating means on a second face of the inert slab for generating a bulk wave toward the first face; and
   sensing means on the slab for generating an output based upon at least one characteristic of the bulk wave, after it has reflected from the first face, said output being a function of viscoelastic properties of the mucous.

2. A device as recited in claim 1 further comprising a comparison means for comparing the output to a reference output whereby viscoelastic properties of the mucous can be determined.

3. A device as recited in claim 1 wherein the first face of the inert slab is approximately flush with the external wall of the probe housing.

4. A device as recited in claim 1 wherein the probe housing has an internal cavity communicable with the second face of the inert slab.

5. A device as recited in claim 1 wherein an impervious seal is formed between the inert slab and the probe housing.

6. A device as recited in claim 5 wherein the probe housing is comprised of a shell and a sealant material which holds the inert slab in the probe housing to form the impervious seal.

7. A device as recited in claim 1 wherein the sensing means is comprised of:
   receiving means on the slab in the path of the bulk wave after it reflects from the first face for receiving the reflected bulk wave and generating an output; and
   comparison means communicating with the receiving means for measuring the amplitude of the output and comparing the output to a reference output whereby the difference between the output and the reference output is a function of viscoelastic properties of the mucous in contact with the first face.

8. A device as recited in claim 7 wherein the second face is parallel and opposite to the first face.

9. A device as recited in claim 7 wherein the acoustic wave generating means comprises an interdigital transducer on the second face, the receiving means comprises an interdigital transducer on the second face, and the slab is formed of a non-piezoelectric material.

10. A device as recited in claim 1 wherein the inert slab is formed of fused silica.

11. A device as recited in claim 1 wherein the acoustic wave generating means comprises a resonator means acoustically coupled to the slab for generating the bulk wave in the slab toward the first face to form a plurality of resonating waves and the sensing means comprises a detecting means on the slab for generating an output from the plurality of resonating waves.

12. A device as recited in claim 11 further comprising means communicating with detection means for measuring changes in Q of individually modulated peaks of the output whereby changes in Q are a function of viscoelastic properties of the mucous in contact with the first face.

13. A device as recited in claim 12 wherein the resonator means and the detection means are the same.

14. A device as recited in claim 11 wherein the resonator means comprises a first metalizing layer in direct contact with the slab, a second metalizing layer, and an intermediate layer of piezoelectric material sandwiched between and in direct contact with the first and second metalizing layers.

15. A device as recited in claim 1 further comprising means for positioning the first face into contact with the cervical mucous.

16. A device for measuring viscoelastic properties of mammalian cervical mucous, comprising:
   an inert slab having a first face exposable to the mucous;
   acoustic wave generating means on a second face of the slab for generating a bulk wave toward the first face;
   receiving means on the slab in the path of the bulk wave after it reflects from the first face for receiving the reflected bulk wave and generating an output;
   comparison means communicating with the receiving means for measuring the amplitude of the output and comparing the output to a reference output whereby the difference between the output and the reference output is a function of viscoelastic properties of the mucous in contact with the first face.

17. The device of claim 16 wherein the second face is parallel and opposite to the first face.

18. The device of claim 17 wherein the slab is formed of a non-piezoelectric material.

19. The device of claim 17 wherein the acoustic wave generating means comprises a first interdigital transducer on the second face.

20. The device of claim 19 wherein the receiving means comprises a second interdigital transducer on the second face.

21. The device of claim 20 wherein the first and second interdigital transducers are each comprised of a pair of electrodes adjacent to each other and in contact with the second face.

22. The device of claim 21 wherein the first and second interdigital transducers are each comprised of a layer of piezoelectric material which is in direct contact with the pair of electrodes and is also in direct contact with the slab.

23. The device of claim 22 wherein the layer of piezoelectric material covers the pair of electrodes.

24. The device of claim 22 wherein the piezoelectric material is zinc oxide.

25. The device of claim 22 wherein the first and second interdigital transducers are each further comprised of a metalization layer which is in direct contact with the layer of piezoelectric material for enhancing the coupling of acoustic energy into the slab.

26. The device of claim 25 wherein the metalization layer covers the layer of piezoelectric material.

27. The device of claim 25 wherein each pair of electrodes is comprised of a first base having a first plurality of equally spaced arms and a second base having a second plurality of equally spaced arms, the spacing between the first and second plurality of arms being identical, the first and second plurality of arms being intertwined but not in direct contact with each other.

28. The device of claim 27 wherein the width of the first and second plurality of equally spaced arms of each pair of electrodes and the spacing between said first and second plurality of equally spaced arms are such that the acoustic wave generating means generates the bulk wave in the slab such that the bulk wave reflects first off of the first face, then off of the second face, again off of the first face and then to the receiving means.

29. The device of claim 27 wherein the inert slab is approximately 0.635 mm thick and the dimensions for the first and second interdigital transducers are approximately 3.10×4.06 mm, the distance between adjacent arms on the same electrode is approximately 0.025 mm, and wherein the device generates waves at about 39.3 degrees to the plane of the first face.

30. A device for measuring viscoelastic properties of mammalian cervical mucous, comprising:
(a) an inert slab having a first face exposable to the mucous;
(b) resonator means acoustically coupled to the slab for generating a bulk wave in the slab toward the first face to form a plurality of resonating waves;
(c) detecting means on the slab for generating an output from the plurality of resonating waves;
(d) measurement means communicating with the detecting means for measuring changes in Q of individually modulated peaks of the output; and
(e) comparison means for comparing the changes in Q of individually modulated peaks of the output to a reference whereby viscoelastic properties of the mucous can be determined.

31. The device of claim 30 wherein the resonator means and the detector means are the same.

32. The device of claim 30 wherein the slab is comprised of fused silica.

33. The device of claim 30 wherein the slab is comprised of a non-piezoelectric material.

34. The device of claim 30 wherein the resonator means comprises a first metalizing layer in direct contact with the slab, a second metalizing layer, and an intermediate layer of piezoelectric material sandwiched in between and in direct contact with the first and second metalizing layers.

35. The device of claim 34 wherein the second metalizing layer covers the intermediate layer of piezoelectric material and is not in direct contact with the first metalizing layer.

36. The device of claim 34 wherein the intermediate layer of piezoelectric material is comprised of zinc oxide.

37. The device of claim 30 wherein the resonator means is coupled to a second face of the slab which is parallel and opposite the first face.

38. A device for measuring viscoelastic properties of mammalian cervical mucous, comprising:

(a) an inert slab of non-piezoelectric material having a first face exposable to the mucous;
(b) an interdigital transducer on a second face of the inert slab parallel and opposite the first face, said interdigital transducer comprising a pair of electrodes adjacent to each other and in contact with the second face, a layer of piezoelectric material which is in direct contact with the pair of electrodes and is also in direct contact with the slab, and a metalization layer which is in direct contact with the piezoelectric material to enhance the coupling of acoustic energy into the slab;
(c) receiving means on the second face of the slab in the path of the bulk wave after it reflects from the first face for receiving the reflected bulk wave and generating an output.

39. A device as recited in claim 38 further comprising comparison means for measuring the amplitude of the output and comparing the output to a reference output whereby the difference between the output and the reference output is a function of viscoelastic properties of the mucous in contact with the first face.

40. A device as recited in claim 39 wherein the inert slab is comprised of fused silica and the layer of piezoelectric material is comprised of zinc oxide.

41. A method of measuring viscoelastic properties of mammalian cervical mucous, comprising the steps of:
placing a first face of an inert slab in contact with the mucous;
generating a bulk wave toward the first face;
generating an output based upon at least one characteristic of the bulk wave after it has reflected from the first face, said output being a function of viscoelastic properties of the mucous.

42. A method as recited in claim 41 wherein the first face is inserted into a mammalian vaginal cavity and positioned in contact with the mucous.

43. A method as recited in claim 42 wherein the first face is inserted into the vaginal cavity near the cervical os.

44. A method as recited in claim 41 comprising the further step of comparing the output to a reference output whereby the viscoelastic properties of the mucous can be determined.

45. A method as recited in claim 44 wherein the output is generated by a receiving means on the slab in the path of the bulk wave after it reflects from the first face and the amplitude of the output is measured and compared to a reference output in a comparison means whereby the difference between the output and the reference output is a function of viscoelastic properties of the mucous in contact with the first face.

46. A method as recited in claim 45 wherein the receiving means comprises an interdigital transducer on a second face of the slab which is parallel and opposite to the first face.

47. A method as recited in claim 41 wherein the bulk wave is generated by an interdigital transducer.

48. A method as recited in claim 47 wherein the interdigital transducer is comprised of a pair of electrodes adjacent to each other and in contact with a second face of the slab, a layer of piezoelectric material which is in direct contact with the pair of electrodes and is also in direct contact with the slab, and a metalization layer which is in direct contact with the piezoelectric material for enhancing the coupling of acoustic energy into the slab.

49. A method as recited in claim 48 wherein the slab comprises a non-piezoelectric material and the second face is parallel and opposite the first face.

50. A method as recited in claim 41 wherein the bulk wave is generated by a resonator means acoustically coupled to the slab and the output is generated by a detection means on the slab by said resonator.

51. A method as recited in claim 50 comprising the further step of measuring changes in Q of individually modulated peaks of the output whereby changes in Q are a function of viscoelastic properties of the mucous in contact with the first face.

52. A method as recited in claim 50 wherein the resonator means and the detection means are the same.

53. A method as recited in claim 50 wherein the resonator means comprises a first metalizing layer in direct contact with the slab, a second metalizing layer, and an intermediate layer of piezoelectric material sandwiched in between and in direct contact with the first and second metalizing layers.

54. A device suitable for measurement of viscoelastic properties of mammalian cervical mucous, comprising:
a probe housing;
an inert slab held in the probe housing, the inert slab having a first face exposable to the mucous;
acoustic wave generating means on a second face of the inert slab for generating a bulk wave toward the first face;
sensing means on the slab for generating an output based upon at least one characteristic of the bulk wave, after it has reflected from the first face, said output being a function of viscoelastic properties of the mucous; and
comparison means for comparing the output to a reference output whereby viscoelastic properties of the mucous can be determined.

55. A device suitable for measurement of viscoelastic properties of mammalian cervical mucous, comprising:
a probe housing;
an inert slab held in the probe housing, the inert slab having a first face exposable to the mucous, the probe housing being shaped for insertion into a mammalian vagina for positioning the first face in contact with the cervical mucous;
resonator means acoustically coupled to the slab for generating a bulk wave in the slab toward the first face to form a plurality of resonating waves;
detection means on the slab for generating an output from the plurality of resonating waves;
measurement means communicating with the detection means for measuring changes in Q of individually modulated peaks of the output, whereby changes in Q are a function of viscoelastic properties of the mucous in contact with the first face.

56. The device of claim 55 wherein the resonator means and the detection means are the same.

57. The device of claim 55 wherein the resonator means is coupled to a second face of the slab which is parallel and opposite the first face.

* * * * *